(12) United States Patent
Farber

(10) Patent No.: US 11,253,533 B1
(45) Date of Patent: *Feb. 22, 2022

(54) WATER DISSOLVABLE MACROCYCLIC LACTONE CYCLODEXTRIN COMPLEXES

(71) Applicant: MOUNTAIN VALLEY MD INC, Vaughan (CA)

(72) Inventor: Michael Farber, Livingston, NJ (US)

(73) Assignee: MOUNTAIN VALLEY MD INC, Vaughan (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/363,375

(22) Filed: Jun. 30, 2021

Related U.S. Application Data

(63) Continuation-in-part of application No. 17/132,203, filed on Dec. 23, 2020, now Pat. No. 11,077,134, which is a continuation-in-part of application No. 17/094,297, filed on Nov. 10, 2020.

(51) Int. Cl.

| | |
|---|---|
| *A61K 31/7048* | (2006.01) |
| *A61K 9/08* | (2006.01) |
| *A61K 47/69* | (2017.01) |
| *A61K 47/26* | (2006.01) |

(52) U.S. Cl.
CPC ............ *A61K 31/7048* (2013.01); *A61K 9/08* (2013.01); *A61K 47/6951* (2017.08); *A61K 47/26* (2013.01)

(58) Field of Classification Search
None
See application file for complete search history.

(56) References Cited

U.S. PATENT DOCUMENTS

| | | | | |
|---|---|---|---|---|
| 4,389,397 A * | 6/1983 | Lo | ............................ | B82Y 5/00 514/53 |
| 11,077,134 B1 * | 8/2021 | Farber | ................... | A61K 31/724 |
| 2002/0032161 A1 * | 3/2002 | Ringshaw | .......... | A61K 31/7048 514/28 |
| 2006/0062817 A1 * | 3/2006 | Cottrell | .............. | A01N 2300/00 424/405 |
| 2011/0268804 A1 * | 11/2011 | Shi | .......................... | A61P 31/00 424/489 |
| 2013/0216820 A1 * | 8/2013 | Riddle | ..................... | C09D 7/63 428/313.9 |

FOREIGN PATENT DOCUMENTS

| | | | | |
|---|---|---|---|---|
| CN | 1206919 C | * | 6/2005 | |
| CN | 100394852 C | * | 6/2008 | |
| CN | 104208017 A | * | 12/2014 | |
| FR | 3042412 A1 | * | 4/2017 | ........... A61K 9/0019 |

OTHER PUBLICATIONS

Cyclolab. "Report for the Preparation of ivermectin/HPBCD inclusion complex (Jul. 2020)." Cyclolab cyclodextrin Research & Development Laboratory Ltd, Jul. 2020, 14 printed pages. (Year: 2020).*

Maria D. Veiga, Fakhrul Ahsan. "Influence of surfactants (present in the dissolution media) on the release behaviour of tolbutamide from its inclusion complex with b-cyclodextrin." European Journal of Pharmaceutical Sciences 9 (2000) 291-299. (Year: 2000).*

Google Patents. English Translation of CN104208017A. https://patents.google.com/patent/CN104208017A/en?oq=CN+104208017+ accessed Aug. 23, 2021, originally published in Chinese on Dec. 17, 2014, 10 printed pages. (Year: 2014).*

Google Patents. English Translation of FR 3042412 A1. https://patents.google.com/patent/FR3042412A1/en?oq=FR+3042412 accessed Aug. 23, 2021, originally published Apr. 21, 2017, 8 printed pages. (Year: 2017).*

Ana M. dos Santos Moreira et al. "Hydrophobic Nanoprecipitates of β-Cyclodextrin/Avermectins Inclusion Compounds Reveal Insecticide Activity against Aedes aegypti Larvae and Low Toxicity against Fibroblasts." Journal of Agricultural and Food Chemistry, vol. 66, 2018, pp. 7275-7285. (Year: 2018).*

Bruce A. Kerwin. "Polysorbates 20 and 80 Used in the Formulation of Protein Biotherapeutics: Structure and Degradation Pathways." Journal of Pharmaceutical Sciences, vol. 97, No. 8, Aug. 2008, pp. 2924-2935. (Year: 2008).*

(Continued)

*Primary Examiner* — Isaac Shomer

(74) *Attorney, Agent, or Firm* — Michael J. Feigin, Esq.; Feigin and Fridman LLC

(57) ABSTRACT

Injectable Ivermectin solution is safely administrable to humans and animals used the disclosed technology. A macrocyclic lactone cyclodextrin complex which is completely dissolvable or dissolved in water in a ratio of at least 5 or 10 mg of macrocyclic lactone to 1 mL of water. The macrocyclic lactone cyclodextrin complex is non-toxic, without using organic solvents, and in embodiments, formed by adding a surfactant to the macrocyclic lactone complex to water. The macrocyclic lactone cyclodextrin complex is Ivermectin or an Ivermectin derivative in some embodiments. The cyclodextrin complex is 2-hydroxypropyl-beta-cyclodextrin in some embodiments of the disclosed technology. The surfactant can be polysorbate 80 and is in a ratio of 0.01% to 25%, by weight, to said water. The water soluble complexes can be added to the water. The water-soluble complexes can have at least one of an anti-parasitic, anti-viral and anti-cancer complex.

12 Claims, No Drawings

(56) References Cited

OTHER PUBLICATIONS

ICI Americas Inc. "The HLB System a time-saving guide to emulsifier selection." ICI Americas Inc., Wilmington Delaware, Revised Mar. 1980, pp. 1-22. (Year: 1980).*
Google Patents. English Translation of CN100394852C. https://patents.google.com/patent/CN100394852C/en?oq=CN100394852 accessed on Dec. 23, 2021, originally published in Chinese on Jun. 18, 2008, pp. 1-6. (Year: 2008).*
Google Patents. English Translation of CN1206919C. https://patents.google.com/patent/CN1206919C/en?oq=CN+1206919 accessed on Dec. 23, 2021, originally published in Chinese on Jun. 22, 2005, pp. 1-6. (Year: 2005).*
Cyclodextrin News. "Avermectin, the Nobel Prize Winner Drug in Cyclodextrin-Enabled Formulations." vol. 30 No. 4, Apr. 2016, ISSN 0951-256X, pp. 1-25, obtained at https://cyclolab.hu/userfiles/cdn_2016_apr.pdf on Dec. 23, 2021. (Year: 2016).*

\* cited by examiner

WATER DISSOLVABLE MACROCYCLIC LACTONE CYCLODEXTRIN COMPLEXES

BACKGROUND

Ivermectin, a macrocyclic lactone, is a substance used to control human filarial infections, onchocerciasis, and lymphatic filariasis, and the only drug used to prevent heartworm in dogs and cats as of the time of this writing. Further, at this time, it is only approved to be taken orally by humans. Ivermectin further has a low solubility in water (about 0.005 mg per ml at 25 degrees Celsius). This makes giving high doses difficult because Ivermectin solution contains a lethal poison (glycerol formal).

Ivermectin and the avermectin family are antiparasitic agents which are useful against endoparasites and ectoparasites in mammals as well as having agricultural uses against various parasites found in and on crops and in soil. Ivermectin is a mixture, in the ratio of approximately 80:20 of 22,23-dihydro C-076 Bla and Blb. In administering Ivermectin to animals, it is most convenient for parenteral formulations to use an aqueous solution. Non-aqueous solutions tend to cause irritation and tissue damage at the injection site; precipitate the active ingredient at the injection site, have higher viscosity and poorer syringability; and generally, have a higher cost. Aqueous liquid formulations, in the prior art, have been used orally.

Ivermectin can be solubilized using surface active agents as solubilizers. This results in the formation of micelles, or minute colloidal particles which surround the Ivermectin molecule, isolating it from the water, but forming a clear solution in the water. Such a solution does contain sufficient active ingredient in order to prepare liquid formulations, for oral or parenteral use. However, it was discovered that such micelle formulations were unstable and the Ivermectin degraded at such a rate as to render the shelf life inadequate for a commercial preparation.

The current state of the art is demonstrated in the following references.

Chinese patent CN104208017A is based on the formation of emulsions using cyclodextrin and ivermectin. The emulsions are not true solutions and use emulsifiers, coemulsifiers, and organic solvents to achieve solubility of water at higher levels.

Bimectin plus injection for cattle described at https://www.bimectin.com/species-exports/cattle/bimectin-plus, accessed Nov. 7, 2020 (with the safety sheet submitted in an Information Disclosure Statement) cannot be used in humans. It is an organic based solvent solution with teratogenic and fetogenic effects of glycerol formal.

U.S. Pat. No. 4,389,397, again requires organic solvents. In this case, use of cyclodextrin is not disclosed. A 7% solubility of Ivermectin is achieved.

FR 3042412 to Alain, et al, discloses a solubilit of ivermectin in an without an organic solvent, however, this reference appears to describe only a maximum concentration of ivermectin of 2 mg per millileter of water.

In summary, what is known to exist today is as follows:
Humans
   Oral tablets—low bioavailability, need for repeated dosing;
   Topical ointment—adverse effects;
   NO injection available for humans
Cattle, Swine
   Injection—only safe for cattle and swine, teratogenic and harmful for humans due to its formulation; highly viscous—needing a 14 to 16 gauge needle
   Tablets—need to be mixed in with food, low bioavailability;
   Pour-on solution—thick, viscous, not effective absorption.

As known by the inventor, there are no truly water-based injectable solution for Ivermectin.

SUMMARY OF THE DISCLOSED TECHNOLOGY

A macrocyclic lactone cyclodextrin complex (herein, "complex") which is completely dissolvable or dissolved in water in a ratio of at least 50 micrograms to 500 milligrams of the macrocyclic lactone complex per 5 milliliters of water. The macrocyclic lactone cyclodextrin complex is non-toxic, without using organic solvents, and in embodiments, formed by adding a surfactant to the macrocyclic lactone complex to water. The macrocyclic lactone cyclodextrin complex is Ivermectin or an Ivermectin derivative in some embodiments. The cyclodextrin complex is 2-hydroxypropyl-beta-cyclodextrin in some embodiments of the disclosed technology. The surfactant can be Polysorbate 80 and is in a ratio of 0.01% to 25%, by weight, such as about 10%, to said water. The water-soluble complexes can be added to the water. The water-soluble complexes have at least one additional component of an anti-parasitic, anti-viral and anti-cancer complex.

The macrocyclic lactone cyclodextrin formed based on some or all of the above description is safely injectable at a dosage of approximately 20 to 400 micrograms per kilogram in an animal selecting the group consisting of swine, cattle, poultry, human, and husbanded animal. In this manner, Ivermectin or Ivermectin derivatives can be administered by way of injection, oral delivery, parenterally, or transmucosally whether through vaginal, rectal, nasal, buccal, ocular or any other mucosal surfaces.

The macrocyclic lactone cyclodextrin complex can also be placed in a solution or a powdered form, into a vial. Water added/mixed therewith is then agitated. A surfactant can be added until the lactone cyclodextrin complex is fully dissolved in the water. In this and other embodiments, 2-hydroxypropyl-beta-cyclodextrin can be up to 12% of a weight or volume of the water increasing solubility of the macrocyclic lactone cyclodextrin complex in said solution by a factor of at least 10 times compared to a solution which lacks a cyclodextrin complex. The factor of solubility can also be 1000 times or higher.

A non-toxic macrocyclic lactone solution which is formed without the aid of and/or presence of organic solvents, is thus created where a macrocyclic lactone cyclodextrin complex and surfactant are completely dissolvable or dissolved in water in a ratio of at least 5 micrograms to 100 milligrams of said macrocyclic lactone to 5 milliliters of water.

The macrocyclic lactone cyclodextrin complex with the surfactant can be in a ratio of at least 5 micrograms to 200 milligrams of the macrocyclic lactone to 5 or 10 milliliters of water. The macrocyclic lactone cyclodextrin complex with the surfactant is completely dissolvable or dissolved in water in a ratio of at least 5 or at least 10 mg of macrocyclic lactone to 1 mL of water in other embodiments of the disclosed technology. This solution can contain other water-soluble or water-miscible substances such as preservatives, antioxidants or other compounds within the scope of the disclosed technology. The solution can also be administered dermally, transdermally, orally, injection, intravenous or transmucosally.

Any device or step to a method described in this disclosure can comprise, or consist of, that which it is a part of, or the parts which make up the device or step. The term "and/or" is inclusive of the items which it joins linguistically and each item by itself. Any element or described portion of the devices shown can be "substantially" as such, if used in the claims in this manner. Where used, "substantially" is defined as "within a 5% tolerance level thereof."

DETAILED DESCRIPTION OF EMBODIMENTS OF THE DISCLOSED TECHNOLOGY

Ivermectin cyclodextrin complex is formed in a manner known in the art, such as with hydroxypropyl or sulfobutylether derived beta cyclodextrins. Any suitable cyclodextrin complex can be used. Formation of these complexes is achieved through any of the number of processes whether solid or liquid solvent-based processes as known in the art wherein the complex has, in some embodiments, 1 mole of Ivermectin per 3 moles of cyclodextrin or 1 mole of Ivermectin per 4 moles of cyclodextrin. Ratios of at least 1 to 3 are used in many embodiments.

When using Ivermectin, the ratio of Ivermectin to 2-hydroxypropyl-beta-cyclodextrin (HPBCD) can be 10% to 20%, such as 13%, by weight of the inclusion complex without water weight. The water-based solution of Ivermectin in embodiments of the disclosed technology consists or comprises of HPBCD, water, and Polysorbate 80 (TWEEN 80), at about 10% or in other embodiments, 20% by weight. The TWEEN 80 can be from 0.01% to 25% by weight of water, such as between and inclusive of 10 to 15% by weight of water. In one embodiment, the TWEEN 80 is 10% by weight. Surfactants used can be cationic, ionic, or non-ionic (such as TWEEN 80). Up to 500 mg of macrocyclic lactone complex is dissolved into 5 ml of Tween 80-distilled water solution. The dissolution of the complex into the TWEEN 80-distilled water can take between 24-48 hours.

Various stabilizers, preservatives, and other additives can also be used. Other non-ionic surfactants or emulsifiers other than TWEEN 80 can be used. All TWEENs and all other human or animal compatible non-ionic surfactants as are known in the art can be used. Such a complex can comprise other substances or consists only of those described in this paragraph and the preceding two paragraphs.

Combinations in solution with other antiparasitic or antiviral or anticancer ingredients, molecules, or combinations are further contemplated to be added to the core invention either as soluble ingredients or water-soluble complexes. The injectable composition can be easily used in both human and animal health either as a prepared solution or as a base powder micronized and filled to appropriate amounts per sealed vial. The sealed vial will then have a solution of water/TWEEN 80. Base powder is added and then the vial is agitated, left for 8 or more hours to settle and/or until complete dissolution. The injectable composition is then ready for injection. Larger multi-dose vials as kits can be prepared in the same manner.

The created concentrate can be injected into a human such as 1 milliliter thereof. The concentrate can be diluted in water or another liquid injectable substance down to 1 part per 100 complex to water. In tests on beagles, an extremely sensitive breed of dog to Tween 80, 0.1% and 0.2% solutions were injected with no noticeable and no known anaphylaxis. As such, about 1% solutions can be used based on data comparing human anaphylaxis to beagle.

The solutions can be prepared in bulk and administered by needless guns such as the Henke Sass Epivag or The Boehringer Ingelheim Freivac used in swine to inject Wimectin. Currently, Ivermectin injectables for animals show ineffective Cmax and Tmax compared to oral delivery due to the highly lipophilic nature of Ivermectin and extremely low water solubility. Both these issues are overcome by way of this technology.

Based on the above, injectable ivermectin solution that can be safely administrated to humans and animals which is unknown in the prior art. This is useful to treat encephalitis, dengue, HIV, ALS, and other diseases. The Ivermectin can also be inhaled for lung cancer, tuberculosis, and possibly for treatment of Covid-19. Spray aerosols can be used to kill insects such as bed bugs or mites. Topical ointment in the form of a cream or 1% gel ointment for skin diseases such as scabies, rosacea, and lice can be treated with the disclosed technology. Eye drops with the disclosed Ivermectin complex can be used to treat ocular infections such as onchocerciasis, and orbital myositis. Gel capsules can be made which are water soluble, have variable absorption, and used to treat diseases such as malaria (affecting millions of people annually). The Ivermectin complex can further be injected into horses and is safer (less toxicity) and more effective than what is known in the art. in a liquid, the Ivermectin complex can be drank by cattle and swine instead of in tablet form as is used in the prior art. In liposomes, the Ivermectin complex can be used to help treat cancer and tumor reactivity.

Macrocyclic is defined as a chemical ring formed from at least 15 atoms. Lactone is defined as cyclic esters formed from hydroxy acids. Cyclodextrin is defined as any of a class of complex cyclic sugars that are products of the enzymatic decomposition of starch and that can catalyze reactions between simpler molecules which come together within the cylindrical body of the sugar. Complex is defined as a chemical association of two or more species (such as ions or molecules) joined usually by weak electrostatic bonds rather than covalent bonds. Dissolvable or dissolved is defined as placed in solution.

Non-toxic is defined as safe to ingest or be introduced into the blood stream at amounts of less than 1000 grams per day without chemically causing damage to the body. "Without" is defined as the ability to cause a desired effect lacking a substance referred to as being "without". An organic solvent is defined as a carbon-based substances capable of dissolving or dispersing one or more other substances. A surfactant is a combination of molecules that spontaneously bond with each other to form sealed bubbles which lower surface tension of a liquid. Ivermectin has a chemical formula of $C_{48}H_{74}O_{14}$ and a molecular weight of 875.1 g/mol. The IUPAC name is (1R,4S,5'S,6R,6'R,8R,10E,12S,13S,14E, 16E,20R,21R,24S)-6'-[(2S)-butan-2-yl]-21,24-dihydroxy-12-[(2R,4S,5S,6S)-5-[(2S,4S,5S,6S)-5-hydroxy-4-methoxy-6-methyloxan-2-yl]oxy-4-methoxy-6-methyloxan-2-yl]oxy-5',11,13,22-tetramethylspiro[3,7,19-trioxatetracyclo[15.6.1.1$^{4,8}$.0$^{20,24}$]pentacosa-10,14,16,22-tetraene-6,2'-oxane]-2-one.

An Ivermectin derivative is a compound that is formed from ivermectin or one which has one atom replaced with another atom or group of atoms.

Ivermectin-HPBCD (2-hydroxypropyl-beta-cyclodextrin) complex, in a trial, was formed by methanol solution refluxing then evaporation. This formed 13% ivermectin in a complex with 87% HPBCD by weight. Polysorbate 80 was added at 110 degrees Fahrenheit to distilled water in a ratio of 1 gram Polysorbate (TWEEN) 80 to 9 grams of distilled water. Dissolution was completed in four hours or less. (Observation took place at four hours.) In testing, 1 gram of ivermectin complex was added to the polysorbate 80-distilled water solution and stirred at 2000 rpm for 5 minutes then left to fully dissolve for 48 hours at 75 degrees Fahrenheit without light. The solutions were diluted and filtered thru a 0.2 micron filter to a mixture of 0.2 milligrams per milliliter ivermectin and 0.1 milligrams per milliliter ivermectin in each of two different respective mixtures. Tests conducted by way of LC/MS/MS. Results show original solution and dilutions to be as predicted. The FD-36 oral tablet averages 400 micrograms per kilogram and achieves a Cmax of 66 nanograms per millimeter after 6 hours. A comparable dose of the present injectable complex would achieve 400 nanogram per milliliter after 15 mins and substantially maintain this ratio without a decrease for at least 6 hours.

Data from trials is below. Therefore, the new injectable solution disclosed herein shows at least a 6:1 increase over the currently available oral form and a 10:1 increase over the currently available subcutaneous form of ivermectin absorption.

In the test study with the Beagles, the graph shows IM injection of IVM is essentially a flat line at 10 ng/ml for a 10 ug/kg injection starting at 15 min and going straight out for 6 hours with little or no declination.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalence of the claims are to be embraced within their scope. Combinations of any of the methods, systems, and devices described herein-above are also contemplated and within the scope of the disclosed technology.

The invention claimed is:

1. A non-toxic macrocyclic lactone solution, without an organic solvent, comprising:

a macrocyclic lactone with a cyclodextrin complex formed into a macrocyclic lactone cyclodextrin complex;

a polysorbate surfactant;

wherein said macrocyclic lactone is an ivermectin or an ivermectin derivative; and wherein said macrocyclic lactone cyclodextrin complex is completely dissolvable or dissolved in water in a ratio of at least 10 mg of macrocyclic lactone to 1 mL of water.

2. The solution of claim 1, wherein said cyclodextrin of said macrocyclic lactone cyclodextrin complex is 2-hydroxypropyl-beta-cyclodextrin.

3. The solution of claim 1, wherein said polysorbate surfactant is polysorbate 80 and is 0.01% to 25%, by weight, of said water.

4. The solution of claim 2, wherein said solution is safely injectable at a dosage of approximately 20 to 400 micrograms per kilogram in an animal selected from the group consisting of swine, cattle, poultry, human, and husbanded animal.

5. The solution of claim 1, formed at least in part by:

placing said macrocyclic lactone cyclodextrin complex, in a solution or a powdered form, into a vial;

adding water to the vial comprising macrocyclic lactone cyclodextrin complex;

adding the polysorbate surfactant to the vial comprising macrocyclic lactone cyclodextrin complex; and agitating said vial while, or after, adding said surfactant until said macrocyclic lactone cyclodextrin complex is fully dissolved in water.

6. The solution of claim 1, wherein said macrocyclic lactone solution is encased in a liposome.

7. The solution of claim 1, wherein said macrocyclic lactone solution is capable of being administered by inhalation.

8. A method of forming a non-toxic macrocyclic lactone solution without the use of organic solvents, comprising:

forming or providing a macrocyclic lactone with a cyclodextrin complex into a macrocyclic lactone cyclodextrin complex wherein said macrocyclic lactone is an ivermectin or an ivermectin derivative;

adding a surfactant to said macrocyclic lactone complex, wherein the surfactant is a polysorbate;

adding water to the macrocyclic lactone cyclodextrin complex;

wherein the macrocyclic lactone cyclodextrin complex with the polysorbate surfactant is completely dissolvable or dissolved in water in a ratio of at least 5 mg of macrocyclic lactone to 1 mL of water.

9. The method of claim 8, wherein said cyclodextrin of said macrocyclic lactone cyclodextrin complex is 2-hydroxypropyl-beta-cyclodextrin.

10. The method of claim 9, wherein said polysorbate surfactant is polysorbate 80 and is in a ratio of 0.01% to 25%, by weight, to said water.

11. The method of claim 9, wherein said solution is safely injectable at a dosage of approximately 20 to 400 micrograms per kilogram in an animal selected from the group consisting of swine, cattle, poultry, human, and husbanded animal.

12. The method of claim 8:

wherein the macrocyclic lactone cyclodextrin complex with the polysorbate surfactant is completely dissolvable or dissolved in water in a ratio of at least 10 mg of macrocyclic lactone to 1 mL of water.

* * * * *